(12) United States Patent
Bonrath et al.

(10) Patent No.: US 8,536,341 B2
(45) Date of Patent: Sep. 17, 2013

(54) PRIMARY ALLYLIC ALCOHOL AND AG

(75) Inventors: Werner Bonrath, Freiburg (DE);
Jean-Francois Eckhard, Paris (FR);
Manfred L. Eggersdorfer, Stein (CH);
Ramona Hinze, Daun (DE); Wolfgang F. Hölderich, Frankenthal (DE);
Michael H. Valkenberg, Leverkusen (DE)

(73) Assignee: DSM IP Assets B.V., Heerlen (NL)

( * ) Notice: Subject to any disclaimer, the term of this patent is extended or adjusted under 35 U.S.C. 154(b) by 638 days.

(21) Appl. No.: 12/526,860

(22) PCT Filed: Feb. 15, 2008

(86) PCT No.: PCT/EP2008/001169
§ 371 (c)(1),
(2), (4) Date: Jul. 20, 2010

(87) PCT Pub. No.: WO2008/098774
PCT Pub. Date: Aug. 21, 2008

(65) Prior Publication Data
US 2011/0015412 A1   Jan. 20, 2011

(30) Foreign Application Priority Data
Feb. 16, 2007  (EP) ..................... 07003307

(51) Int. Cl.
*C07D 211/94* (2006.01)
*C07C 29/56* (2006.01)
(52) U.S. Cl.
USPC .......................................... 546/184; 568/906

(58) Field of Classification Search
USPC .......................................... 546/184; 568/906
See application file for complete search history.

(56) References Cited

U.S. PATENT DOCUMENTS
6,686,485 B2   2/2004  West

FOREIGN PATENT DOCUMENTS
GB          03543        0/1904
WO       01/42177       6/2001

OTHER PUBLICATIONS

Cecchetto et al. "Efficient Mn-Cu and Mn-Co-TEMPO-catalysed oxidation of alcohols into aldehydes and ketones by oxygen under mild conditions" Tetrahedron Letters, 2001, vol. 42, No. 38, pp. 6651-6653.*
International Preliminary Report on Patentability dated Aug. 27, 2009.
International Search Report for PCT/EP2008/001169, mailed Jun. 4, 2008.
Cecchetto et al., "Efficient Mn-Cu and Mn-Co-TEMPO-Catalysed Oxidation of Alcohols into Aldehydes and Ketones by Oxygen Under Mild Conditions", Tetrahedron Letters, Elsevier, Amsterdam, vol. 42, No. 38, Sep. 17, 2001, pp. 6651-6653, XP004317837.

* cited by examiner

*Primary Examiner* — Joseph Kosack
(74) *Attorney, Agent, or Firm* — Nixon & Vanderhye P.C.

(57) ABSTRACT

The invention relates to a process of reacting a primary allylic alcohol with a compound containing a) a metal selected from the group consisting of Ag, Au, Ce, Mn, Ni, Ru, Re, Zn and Co preferably Ag and b) an oxidant like TEMPO (2,2',6,6'-tetramethylpiperidin-1-oxyl) or its derivates and c) a co-oxidants selected from the group of peroxodisulfates (PDS), $H_2SO_5$, $H_2O_2$, NaOCl, $O_2$, KOCl, and air.

26 Claims, No Drawings

PRIMARY ALLYLIC ALCOHOL AND AG

This application is the U.S. national phase of International Application No. PCT/EP2008/001169, filed 15 Feb. 2008, which designated the U.S. and claims priority to Europe Application No. 07003307.1, filed 16 Feb. 2007, the entire contents of each of which are hereby incorporated by reference.

The synthesis of vitamins and carotenoids is industrially very important. Some key intermediates are primary and tertiary allylic alcohols. The production of linalool from geraniol and/or nerol is one of these industrially important reactions. One synthesis of isophytol starts from citral, which is transformed by hydrogenation to nerol/geraniol followed by rearrangement to linalool. Linalool itself is C3-elongated to geranyl acetone by Carroll reaction. The transformation of geraniol/nerol into linalool is normally catalyzed by a tungsten catalyst. Disadvantage in many of these catalytic reactions is the low yield and/or selectivity. Another possibility would be the use of homogeneous acids, however, those may cause environmental problems.

SUMMARY OF THE INVENTION

It now has been found that reacting a primary allylic alcohol with a compound containing a metal selected from the group consisting of Ag, Au, Ce, Mn, Ni, Ru, Re, Zn and Co preferably Ag and an oxidant like TEMPO (2,2',6,6'-tetramethylpiperidin-1-oxyl) or its derivates and a co-oxidants selected from the group of peroxodisulfates (PDS), $H_2SO_5$, $H_2O_2$, NaOCl, $O_2$, KOCl, and air can improve that situation.

In WO 2005/084800 it was reported by Johnson Matthey that reacting TEMPO (2,2',6,6'-tetramethylpiperidin-1-oxyl) supported on polymers leads to an oxidation of primary alcohols such as octanol.

Similar reaction conditions (TEMPO, peroxodisulfate in aqueous phase, Ag based catalyst) have been reported for the treatment of sugars in J. Catal. 2000, 194, 345-351 (Hölderich et al).

It can be observed that the alcohols behaved differently in presence of supported TEMPO in comparison with free TEMPO under similar oxidizing conditions.

Surprisingly, for geraniol using the TEMPO supported on polymer catalyst, it appears that the main products were: 3,7-dimethyl-1,6-octadien-3-ol=linalool (selectivity: 47.7%) and 3,7-dimethyl-6-octen1-ol (selectivity: 40.6%) with a conversion of 70.4% (Tables 1 and 2, Nr. JE 280). These two products could come from a rearrangement reaction of the geraniol structure.

It has to be looked upon as very surprising that a primary alcohol in the presence of an oxidation system does not primarily lead to regular oxidation products such as aldehydes or acids, but to other industrially very important intermediates.

SUMMARY OF THE INVENTION

The invention relates to a process comprising reacting a primary allylic alcohol with a compound containing a metal selected from the group consisting of Ag, Au, Ce, Mn, Ni, Ru, Re, Zn and Co preferably Ag and an oxidant like TEMPO (2,2',6,6'-tetra-methylpiperidin-1-oxyl) or its derivates and a co-oxidants selected from the group of peroxodisulfates (PDS), $H_2SO_5$, $H_2O_2$, NaOClO, $O_2$, KOCl, and air.

In a preferred embodiment of the process the reagent contains PDS. In one embodiment PDS is present in 0.01 to 0.8 mol/l preferably 0.1-0.5 mol/l.

In a preferred embodiment of the process the reagent is TEMPO. It can be observed that the primary allylic alcohols behaved differently in presence of polymer supported TEMPO (PS-TEMPO) in comparison with free TEMPO under similar oxidizing conditions. In the following the term encompassed both species.

In a preferred embodiment of the process PS-TEMPO is used as synthesized according to WO 2005/084800.

In another preferred embodiment of the process the material can be used as commercially available from FLUKA.

In several examples of the invention preferably 1-5 g/l PS-TEMPO was used. In a preferred embodiment the catalyst loading was between 2 to 15 mmol/g.

In another embodiment of the invention a TEMPO species was used in an amount of between $0.5 \times 10^{-3}$ mmol to $15 \times 10^{-3}$ mmol TEMPO per mmol of primary allylic alcohol.

In a preferred embodiment of the process the compound is a salt, salt such as nitrate, sulfate and carbonate, preferably a basic salt, more preferably a carbonate.

In a preferred embodiment of the process the compound is a silver salt or silver on a carrier. One useful amount of silver salt or silver on a carrier to be used is between 1 to 20 mg Ag per gram of primary allylic alcohol.

In a preferred embodiment of the process the compound is a catalyst, preferably a heterogeneous catalyst with a surface area of more than 50 $m^2/g$ preferably of between 50 and 600 $m^2/g$, more preferably of between 50 and 250 $m^2/g$.

Suitable catalysts include:

Ag-γ-$Al_2O_3$

Ag—SiO2

Ag-Celite

The catalyst can be supported by a carrier. Carriers which can be used successfully in the invention can be selected from the group of $Al_2O_3$, $SiO_2$, zeolites, celite, hydrotalcite, mesoporous materials of the MS-group (such as MCM41 or MCM48) more preferably, hydrotalcite and celite which contains $CO_3$ anions and most preferably $Al_2O_3$.

In one embodiment the catalyst is contained in a concentration between 1 to 250 mg metal per gram of catalyst, preferably 10 to 250 mg metal, more preferably 10 to 150 mg metal per gram and most preferably 50-100 mg metal per gram catalyst.

If the metal is to be used together with the PDS it can be used in amounts of 10-1000 mg PDS per mg catalyst. Preferably 100 to 500 mg PDS per mg catalyst is used.

In a preferred embodiment of the process the reaction is carried out at a temperature of at least 0° C., preferably at least 15° C., more preferably 30° C., most preferably at least 60° C.

In a preferred embodiment of the process the reaction is carried out at a temperature not higher than 150° C., preferably not higher than 120° C., more preferably not higher than 100° C. and most preferably not higher than 80° C.

In a preferred embodiment of the process the reaction is carried out at a pressure above atmospheric pressure, preferably above 2 bar, more preferably above 3 bar and most preferably above 5 bar.

In a preferred embodiment of the process the allylic alcohol contains 5-60 C atoms, preferably 5-25 C-atoms, preferably selected from the group consisting of phytol, decaprenol, isodecaprenol, geraniol, nerol, farnesol, nerolidol and solanisol.

In a preferred embodiment of the process the reaction comprises a rearrangement, preferably an isomerization.

In a preferred embodiment a solvent is used. A preferred solvent is water or toluene. In another preferred embodiment a mixture of water and one solvent selected from the group toluene, dichloromethane, methanol, hexane, acetic acid, THF and ionic liquids, most preferable toluene is used.

In still another embodiment of the invention a mixture of water with water-insoluble organic solvents may be used. Examples of water-insoluble organic solvents include aromatic hydrocarbons, aliphatic hydrocarbons, preferably toluene.

In one embodiment of the invention the ratio of water to organic solvent is at least 100:1. In another embodiment the ratio is not more than 100:1, preferably 50:1, more preferably 20:1 and most preferably 10:1.

In a preferred embodiment of the process the reaction product is isolated.

In a preferred embodiment of the process the reaction product comprises at least one tertiary alcohol, preferably to an extent of more than 20% selectivity based on the weight of the reaction products, more preferably more than 50% and most preferably more than 70% selectivity.

In a preferred embodiment of the process the yield is at least more than 5% based on the reactants, preferably more than 10 and most preferably between 10 and 20%.

In a preferred embodiment of the process the yield is not more than 50% based on the reactants, preferably not more than 40% and most preferably not more than 30%.

In a preferred embodiment of the process the yield is not more than 50% based on the educts, preferably not more than 40% and most preferably not more than 30%.

In a preferred embodiment of the process the reaction product is reacted to vitamin A, vitamin E, a carotinoid, an ubiquinone or a flavor compound.

In a preferred embodiment of the process the reaction product is reacted to beta carotene or canthaxanthin.

In a preferred embodiment of the process the reaction product is reacted to nerolidol.

It can be observed that the three alcohols behaved differently in presence of supported TEMPO in comparison with free TEMPO under similar oxidizing conditions.

Another catalytic system was also applied to these reactions. It was formed out of a metal salt immobilized in an ionic liquid supported on silica.

Other catalysts for this reaction are a Zn—Ru—Al-hydrotalcite or Mn on alumina. These catalysts have a low activity, but high selectivity.

Other possible applications are isomerizations of phytol to isophytol, decaprenol to isodecaprenol, vitamin A, isomerization of solanisol (important for CoQ10).

EXAMPLES

Several embodiments of the invention are further described in the following examples.

General Preparation Procedure of a Suitable Catalyst

To a suitable silver salts in water the carrier material was added and the mixture was stirred for 15 h at room temperature. The solids were filtered and dried for 2 h at 120° C.

After that the resulting solid was heated for 10 h at 500° C. The heating and cooling rate of the oven was chosen to be 10° C./min.

| Silver salt | Carrier material | Solvent |
|---|---|---|
| 0.31 g AgNO$_3$ | 5.03 g Al$_2$O$_3$ (D10/10 sales product of BASF AG, Ludwigshafen DE) | 100 ml H$_2$O |
| 0.72 g Ag$_2$CO$_3$ | 5.05 g Al$_2$O$_3$ (D10/10 sales product of BASF AG, Ludwigshafen DE | 100 ml H$_2$O |
| 1.60 g Ag$_2$CO$_3$ | 13.84 g Al$_2$O$_3$ (Alox C sales product of Degussa AG, Hanau DE) | 350 ml H$_2$O |
| 1.60 g Ag$_2$CO$_3$ | 13.79 g Al$_2$O$_3$ (Alox C sales product of Degussa AG, Hanau DE) | 350 ml H$_2$O |
| 3.0 g AgNO$_3$ | 13.0 g Al$_2$O$_3$ (Alox C sales product of Degussa AG, Hanau DE) | 350 ml H$_2$O |
| 5.85 g Ag$_2$CO$_3$ | 60.0 g Al$_2$O$_3$ | 1300 ml H$_2$O |
| 5.93 g Ag$_2$CO$_3$ | 59.91 g Al$_2$O$_3$ (Alox C sales product of Degussa AG, Hanau DE) | 1300 ml H$_2$O |
| 2.0 g AgNO$_3$ | 13.99 g SiO$_2$ | 350 ml H$_2$O |
| 2.0 g Ag$_2$CO$_3$ | 14.50 g SiO$_2$ | 350 ml H$_2$O |

In a variation of this procedure 1 g of the resulting solid was stirred in 10 ml THF and 0.6 g of 4-acetamido-TEMPO was added. During an hour 5 ml TEOS in 10 ml THF were added dropwise to the solution and the resulting mixture was stirred for 5 h at 60° C. After filtration the solid was extracted in a Soxhlet extractor for 24 h with THF.

In another embodiment of the invention the catalyst was prepared as follows

To a solution of 20 ml H$_2$O and 10 ml concentrated NH$_3$ the following components were added under stirring at room temperature: 2 ml TEOS and 5 ml APTMS.

The resulting mixture was stirred for 24 h at room temperature. A slightly turbid solution was formed with a small residue of white solid on the vessels fringes. The solvent was removed in a rotary at 80° C. The resulting solid was dried in an oven for 9 h at 160° C. resulting in 0.6 g of a slightly yellow white powder.

0.5 g of that powder were stirred in 6 ml formaldehyde for 2 h at 60° C. A yellow solid was formed, filtered and dried for 3 h at 120° C. resulting in 0.27 g of a solid.

0.2 g of that solid were added to a solution of 0.013 g AgNO$_3$ and 8 ml H$_2$O and strirred for 2 h at 60° C. The mixture turns brown to black. After further filtration a clear solution and 0.11 g of a brown solid were obtained.

Example 1

Reaction of Geraniol Using TEMPO Supported on Polymer in Acetic Acid 0.102 g of TEMPO supported on polymer, as well as 58 mg of Co(NO$_3$)$_2$, 79 mg of Mn(CH$_3$COO)$_2$ were weighted in a schlenk tube. The schlenk tube was purged several times with pure oxygen. Then 10 ml of AcOH and 1 ml of geraniol were added. The schlenk was heated to 40° C. under an oxygen atmosphere.

Example 2

Reaction of Geraniol in (Organic Phase, Water, PDS, Heterogeneous Catalyst)

36 mg of TEMPO, 2.4 g of PDS, 17 mg of Ag—CO$_3$-γ-Al$_2$O$_3$ were weighted in a round bottom flask. 10 ml of solvent and 2 ml of geraniol were added. The reaction was performed under air atmosphere.

TABLE 1

Catalyst Loading before and after the reaction

| | Catalyst Loading before the reaction mg Ag/g Kat | Catalyst Loading before the reaction mg Ag/g Kat* | PDS | PS-TEMPO |
|---|---|---|---|---|
| Control 1 | 68.3 | 43.6 | X | X |
| Control 2 | 68.3 | 59.0 | X | — |
| Control 3 | 68.3 | 58.5 | — | — |

The catalyst loading stays fairly constant during the reaction. Several control experimgent were run (3.2 ml Geraniol, 15 mg Ag/Al$_2$O$_3$, 0.1 g PS-TEMPO, 5 g PDS, 50 ml water, 80° C., 24 h) to determine the stability. Additionally thermogravimetric measurements established that there is no organic residue on the catalyst after the reaction*

Example 3

Reaction of Alcohols in Organic Phase, Aqueous Phase, Heterogeneous Catalyst 36 mg of TEMPO, 2.4 g of PDS, 17 mg of catalyst were weighted in a round bottom flask. 10 ml of water, 20 ml of AcOEt and 2 ml of substrate were added. The reaction was performed under air atmosphere.

TABLE 2

Influence of different metals in the catalyst

| | Metal Component | Turnover (%) | Selectivity (%) with respect to linalool |
|---|---|---|---|
| Metal1 | Mn—Al$_2$O$_3$ | 23.4 | 71.7 |
| Metal2 | Fe—Al$_2$O$_3$ | 3.3 | >99 |
| Metal3 | Co—Al$_2$O$_3$ | 12.1 | 62.2 |
| Metal4 | Ni—Al$_2$O$_3$ | 32.0 | 48.0 |
| Metal5 | Cu—Al$_2$O$_3$ | 0 | 0 |
| Metal6 | Ru—Al$_2$O$_3$ | 9.8 | 64.7 |
| Metal7 | Ce—Al$_2$O$_3$ | 18.5 | 46.6 |
| Metal8 | Ag/Al$_2$O$_3$ | 74.0 | 42.3 |

(Reaction conitions: 0.6 g Geraniol, 0.003 g Me-Katalysator, 0.02 g PS-TEMPO, 1 g PDS, 10 ml water, 80° C., 2 h)

Example 4

5 g of PDS, 01.g PS TEMPO (Fluka), 15 mg Ag/Al$_2$O$_3$ in a mixture of 50 ml H$_2$O and 25 ml toluene was heated in an oil bath at 80° C. together with 15 mmol of farnesol. After 150 minutes, 8% of nerolidol was recovered.

The invention claimed is:

1. A process comprising reacting a primary allylic alcohol in the presence of a reaction system comprised of (a) a catalyst material containing a metal or metal salt selected from the group consisting of Ag, Au, Ce, Mn, Ni, Ru, Re, Zn, Co and salts thereof, (b) an oxidant selected from the group consisting of 2,2',6,6'-tetra-methylpiperidin-1-oxyl (TEMPO) and polymer supported 2,2',6,6'-tetra-methylpiperidin-1-oxyl (PS-TEMPO), and (c) a co-oxidant selected from the group consisting of peroxodisulfates (PDS), H$_2$SO$_5$, H$_2$O$_2$, NaOCl, O$_2$, KOCl, and air to form a reaction product comprised of at least one tertiary alcohol.

2. The process of claim 1, wherein the co-oxidant is PDS which present in an amount of 0.01 to 0.8 mol/l.

3. The process of claim 1, wherein the oxidant is PS-TEMPO comprising between 2 to 15 mmol/g of TEMPO supported on the polymer and wherein the PS-TEMPO is present in the reaction system in an amount of 1-5 g/l.

4. The process of claim 1, wherein the catalyst material comprises a salt selected from the group consisting of nitrate salts, sulfate salts and carbonate salts.

5. The process of claim 1, wherein the catalyst material is a Ag salt or Ag on a carrier, and is present in an amount of between 1 to 20 mg Ag per gram of primary allylic alcohol.

6. The process of claim 1, wherein the catalyst material is a heterogeneous catalyst with a surface area of more than 0.5 m$^2$/g.

7. The process of claim 4, wherein the catalyst material is supported by a carrier selected from the group consisting of Al$_2$O$_3$, SiO$_2$, zeolites, celite, hydrotalcite, and mesoporous materials.

8. The process of claim 4, wherein the reaction is carried out at a temperature of at least 0° C.

9. The process of claim 8, wherein the reaction is carried out at a temperature not higher than 150° C.

10. The process of claim 1 wherein the reaction is carried out at a pressure above atmospheric pressure.

11. The process of claim 1, wherein the allylic alcohol contains 5-60 carbon atoms.

12. The process of claim 1 wherein the reaction comprises a rearrangement.

13. The process of claim 1, wherein the reaction system further comprises a solvent.

14. The process of claim 13, wherein the solvent is present in the reaction system in a ratio of 100:1.

15. The process of claim 1, further comprising isolating the reaction product from the reaction system.

16. The process of claim 15, wherein the reaction product comprises at least one tertiary alcohol to an extent of more than 20% selectivity based on the weight of all reaction products.

17. The process of claim 16, wherein the tertiary alcohol is present in a molar ratio in relation to other reaction products of 20:80.

18. The process of claim 15, wherein the yield of the reaction product is at least more than 5% based on reactants.

19. The process of claim 18, wherein the yield is not more than 50% based on the reactants.

20. The process of claim 15, further comprising reacting the reaction product to form vitamin A, vitamin E, a carotinoid, an ubiquinone or a flavor compound.

21. The process of claim 20, wherein the carotinoid is beta carotene or canthaxanthin.

22. The process of claim 20, wherein the flavor compound is nerolidol.

23. The process of claim 11, wherein the allylic alcohol contains 5-25 carbon atoms.

24. The process of claim 11, wherein the allylic alcohol is selected from the group consisting of phytol, decaprenol, isodecaprenol, geraniol, nerd, farnesol, nerolidol and solanisol.

25. The process of claim 12, wherein the reaction comprises an isomerization.

26. The process of claim 2, wherein the PDS is present in an amount of 0.1-0.5 mol/l.

* * * * *